(12) United States Patent
Serban et al.

(10) Patent No.: US 7,667,191 B2
(45) Date of Patent: Feb. 23, 2010

(54) DEFORMABLE PHANTOM APPARATUS

(75) Inventors: Monica Serban, Montreal (CA);
Gabriela Stroian, Verdun (CA); Emily Heath, Heidelberg (DE); Jan Seuntjens, Pointe-Claire (CA)

(73) Assignee: McGill University, Montreal, Quebec (CA)

(*) Notice: Subject to any disclaimer, the term of this patent is extended or adjusted under 35 U.S.C. 154(b) by 82 days.

(21) Appl. No.: 12/129,095

(22) Filed: May 29, 2008

(65) Prior Publication Data
US 2008/0298540 A1    Dec. 4, 2008

Related U.S. Application Data

(60) Provisional application No. 60/924,697, filed on May 29, 2007.

(51) Int. Cl.
*G12B 13/00* (2006.01)
(52) U.S. Cl. .................................. 250/252.1
(58) Field of Classification Search .............. 250/252.1
See application file for complete search history.

(56) References Cited

U.S. PATENT DOCUMENTS

| 4,646,334 | A  | * | 2/1987 | Zerhouni ............. 378/18 |
| 5,719,916 | A  |   | 2/1998 | Nelson et al. |
| 6,744,039 | B1 | * | 6/2004 | DiFilippo ............ 250/252.1 |
| 2003/0045803 | A1 | * | 3/2003 | Acharya ............. 600/508 |
| 2003/0220718 | A1 | * | 11/2003 | Jaszczak et al. ........ 700/282 |
| 2005/0211889 | A1 |   | 9/2005 | Varchena et al. |
| 2007/0140413 | A1 |   | 6/2007 | Saracen |
| 2007/0286331 | A1 | * | 12/2007 | Keall et al. ............. 378/8 |
| 2008/0078235 | A1 | * | 4/2008 | Vija et al. ............... 73/37 |
| 2008/0097184 | A1 | * | 4/2008 | Vija et al. ............. 600/407 |

FOREIGN PATENT DOCUMENTS

WO    2007/064951 A2    6/2007

OTHER PUBLICATIONS

Tiezhi Zhang, et al., Treatment plan optimization incorporating respiratory motion, Medical Physics Jun. 2004, pp. 1576-1586. vol. 31, No. 6.
Rojano Kashani, et al., Technical note: A deformable phantom for dynamic modeling in radiation therapy, Medical Physics, Jan. 2007, pp. 199-201, vol. 34, No. 1.

* cited by examiner

*Primary Examiner*—David P Porta
*Assistant Examiner*—Mindy Vu
(74) *Attorney, Agent, or Firm*—Dinsmore & Shohl LLP (57) ABSTRACT

A deformable phantom apparatus for simulating motion of a patient's anatomy in 3D during breathing, the apparatus comprising a chamber fillable with a first fluid, a deformable member comprising tissue equivalent material of the anatomy being simulated, the deformable member being positionable within the chamber in the first fluid and having an open end in fluid communication with a second fluid outside the chamber in use; and a mechanism for causing the second fluid to flow through the open end to deform the deformable member between a normal state and a deformed state to simulate motion during breathing.

33 Claims, 8 Drawing Sheets

DEFORMABLE PHANTOM APPARATUS

CROSS REFERENCE TO RELATED APPLICATION

The Applicants hereby claim priority from U.S. patent application No. 60/924,697 filed 29 May 2007, the contents of which are hereby incorporated by reference in its entirety.

FIELD OF THE INVENTION

The present invention concerns a deformable phantom apparatus for simulating motion of a patient's anatomy, such as a lung, during breathing.

BACKGROUND OF THE INVENTION

Radiotherapy uses ionizing radiation to treat or destroy cancerous tumours and lesions. The damage to tumour cells from the radiation is related to the absorbed dose (i.e., energy absorbed from ionizing radiation per unit mass). Therefore increasing the dose to the tumour increases the number of treated or destroyed cancer cells. However, as higher dose levels may also affect healthy tissue and other structures surrounding the tumour, the amount of ionizing radiation used must be controlled to provide as high as possible a dose to the tumour site whilst minimizing damage to the surrounding healthy tissue.

In three-dimensional conformal radiotherapy (3-D-CRT), a high dose of ionizing radiation is delivered to a tumour volume encompassing the tumour whilst delivering as low as possible a dose outside of this volume. This technique relies on accurately determining the location, size and shape of a tumour, planning the required radiation dose and delivery in order to effectively treat the tumour whilst minimizing complications related to the surrounding healthy tissue.

During the irradiation of intra-thoracic or near thoracic tumours or lesions, respiration can have a significant impact on the tumour location, shape and size and can therefore be a major contributor to the uncertainty in dose delivered to these tumours. It is understood that respiration can affect target and organ movements by as much as 12 mm in a cranio-caudal direction, 5 mm in a medio-lateral direction and 5 mm in a dorso-ventral direction.

Imaging techniques such as computed tomography (CT), magnetic resonance imaging (MRI) scans and other imaging methods have been used to attempt to locate tumours for the planning and execution of radiotherapy treatment, as well as for the calibration of the radiation delivery system prior to delivering a prescribed radiation to a patient. Typically, the location of a tumour is defined relative to implanted or anatomical markers. In CT scanning, for example, the three-dimensional anatomical description of the patient is acquired during free breathing and is used for planning the radiotherapy. However, this technique is affected by motion artefacts on the resultant images which makes localization of the tumour, and therefore the estimation of the dose to be received by the patient, prone to errors and inaccuracies.

Phantoms, defined as structures that contain one or more tissue substitutes used to simulate interactions and/or image properties of organs in the human body, are critical in the testing of the performance of imaging equipment, for measuring radiation dose during therapy and adjusting the real treatment accordingly, for interventional image guided procedures and for quality assurance testing.

One such lung phantom is described in U.S. Pat. No. 5,719,916 which is made of a spongy foam material having the desired x-ray opacity to simulate a human lung. It is placed in a torso cavity of a chest phantom on which breast phantoms can be adjustably attached. These phantoms are for calibrating mammography and x-ray equipment and as the torso cavity and the chest phantom are stationary, motion effects due to a patient breathing are not taken into account.

The recent emergence of four-dimensional radiotherapy, which is defined as "the explicit inclusion of the temporal changes of anatomy during the imaging, planning and delivery of radiotherapy", necessitates phantom apparatus which can track the temporal changes of the anatomy during radiotherapy.

One such phantom apparatus is described in WO 2007/064951, which describes a human-like skeletal structure, deformable organ phantoms in the skeletal structure and a respiration actuator which is positioned to deform the deformable lung phantom with a respiration-like motion. The respiration phantom can be used to determine the amount of radiation exposure to a volume of interest during simulated breathing. In one embodiment, the respiration actuator includes a motor coupled to a push rod and a push plate to reciprocally compress the deformable organ phantoms in the skeletal structure along an inferior to superior axis. This causes the organ phantoms to simultaneously expand or bulge along a posterior to anterior axis and to press against a ribcage of the human-like skeletal structure. However, this mechanism may not impart a physiologically correct movement of the organs during breathing.

Therefore, there is a need for an improved phantom apparatus which can simulate temporal anatomical changes.

SUMMARY OF THE INVENTION

The present invention reduces the difficulties and disadvantages of the aforementioned designs and provides an apparatus which can more accurately and more reproducibly simulate the motion of a patient's anatomy during breathing. Applicants have discovered a deformable phantom apparatus which simulates movement of a patient's anatomy, e.g. an organ, during breathing. Surprisingly, the Applicants have found that the deformable phantom apparatus is highly reproducible and simulates anatomical motion anthropomorphically and in a very close manner to the in vivo situation. The deformable phantom apparatus can find application in four-dimensional (4-D) radiation therapy and aid the management of the respiratory motion in quality assurance for dynamic imaging, treatment planning and dose delivery in radiation therapy.

According to one embodiment of the present invention, there is provided a deformable phantom apparatus for simulating motion of a patient's anatomy in 3D during breathing, the apparatus comprising: a chamber fillable with a first fluid, a deformable member comprising tissue equivalent material of the anatomy being simulated, the deformable member being positionable within the chamber in the first fluid and having an open end in fluid communication with a second fluid outside the chamber in use; and a mechanism for causing the second fluid to flow through the open end to deform the deformable member between a normal state and a deformed state to simulate motion during breathing.

Advantageously, the deformable member can include at least one marker having a different imaging property than the tissue equivalent material. This may be helpful in image registration.

In one embodiment, the deformable phantom comprises a core portion and a cover portion, the core and cover portions being deformable. The core portion can be a porous material, such as a spongey material, which is in a compressed state in the cover portion when the deformable member is in the normal state.

The mechanism can comprise a moveable wall of the chamber connectable to an actuator to drive movement of the moveable wall to cause the second fluid to flow through the open end of the deformable member. The mechanism can also include the actuator which can be a motor. Alternatively, the mechanism can be a drive or an actuator for forcing the second fluid through the open end of the deformable member.

The deformable phantom is attachable to the moveable wall of the chamber such that the deformable phantom is elongated in at least one direction in the deformed state.

The deformable member can further comprise a deformable mass for simulating a tumour or a lesion, the deformable mass being positionable in the tissue equivalent material. The deformable mass comprises tumour or lesion equivalent material. A radiation detector may be provided which is locatable in the deformable mass for radiation measurements.

The first fluid can be a liquid such as water and the second fluid can be a liquid or a gas, such as air.

Advantageously, the patient's anatomy being simulated is within or around the thoracic cavity such as a lung.

From another aspect, there is provided a deformable phantom apparatus for simulating motion of a patient's lung in 3D during breathing, the apparatus comprising: a chamber fillable with a first fluid, a deformable lung phantom comprising lung tissue equivalent material, the lung phantom being positionable within the chamber in the first fluid and having an open end in fluid communication with a second fluid outside the chamber in use; and a mechanism for varying the pressure in the chamber or in the lung phantom to cause the second fluid to flow through the open end to deform the lung phantom between a normal state and a deformed state simulating lung motion during breathing.

The lung phantom can include at least one marker having a different imaging property than the tissue equivalent material, the at least one marker simulating the vascular and bronchial bifurcations of the lung.

The lung phantom comprises a core portion and a cover portion, the core and cover portions being deformable. The core portion can be a porous material, such as a spongey material, which is in a compressed state in the cover portion when the lung phantom is in the normal state.

In one embodiment, the mechanism comprises a moveable wall of the chamber connectable to an actuator to drive movement of the moveable wall to vary the pressure in the chamber. An actuator, such as a motor, connectable to the moveable wall may be provided.

Optionally, the lung phantom is attachable to the moveable wall of the chamber so that the lung phantom is elongated in at least one direction in the deformed state.

The lung phantom may further comprises a deformable mass for simulating a tumour or a lesion, the deformable mass being disposed in the tissue equivalent material and being movable between the normal and deformed states. A radiation detector may be locatable in the deformable mass for dose measurements.

The first fluid can be water and the second fluid can be air.

The deformable phantom apparatus may further comprise a perforated end-piece receivable in the open end of the lung phantom.

From yet another aspect, there is provided a deformable phantom comprising tissue equivalent material, the lung phantom being positionable within a chamber filled with a first fluid and having an open end in fluid communication with a second fluid outside the chamber in use; wherein the deformable phantom is configured to move between a normal state and a deformed state as pressure on or in the deformable phantom is varied, to simulate lung motion during breathing.

The deformable phantom can comprise a core portion and a cover portion, the core and cover portions being deformable. The core portion can be a porous material which is in a compressed state in the cover portion when the deformable member is in the normal state. In one embodiment, the cover portion is a rubber balloon and the core portion is a spongey material.

The deformable phantom can include at least one marker positionable within the tissue equivalent material having a different imaging property than the tissue equivalent material. It can also optionally include at least one deformable mass positionable within the tissue equivalent material for simulating a tumour or a lesion.

From yet a further aspect, there is provided use of a deformable phantom apparatus or deformable phantom as defined above for performing quality assurance of adaptive 4D or non-adaptive radiotherapy delivery.

Advantageously, the deformable member of the phantom apparatus of the present invention can be made of simple and cheap materials such as natural sponge and rubber. The deformable member and the phantom apparatus can be easily and cheaply constructed and used in many methods that deal with the investigation and minimization of the impact of respiratory motion such as: motion-encompassing methods, respiratory gating techniques, and real-time tumour-tracking techniques. One possible application is in 4D radiation therapy. Other possible applications exist in radiology whenever time dependent imaging is required on anatomically realistic representations of the human body.

Since the newest challenge in modern, high-precision intensity-modulated therapy is to deliver the prescribed intensity profile to a moving target, the deformable phantom apparatus of the present invention can evaluate and compensate for organ motion effects and patient positioning errors in radiation therapy. While analytical models and patient data are useful, a reproducible, anthropomorphic, tissue-equivalent deformable phantom such as that of the present invention is critical to proper commissioning and use of new systems for physiological motion management in radiation therapy.

Advantageously, the inclusion of a deformable mass in the deformable member can realistically simulate the presence and movement of a tumour or lesion during breathing. In the case of the lung, tumours inside the lung are known to move significantly due to respiratory movement. By means of the deformable mass being incorporated within the deformable member, the complex 3D trajectory of a real-life tumour can be simulated and tracked. Simulation of hysteresis in the tumour motion can be achieved by regulating the flow of fluid in and out of the deformable member using valves, for example, or by dynamically blocking and unblocking a number of openings in mouth of the cover portion of the deformable member. A compensation may then be incorporated into the radiotherapy treatment to accommodate this movement.

Advantageously, anatomical sub-features, such as vascular and bronchial bifurcations in a lung using Plexiglas™ beads and Nylon™ strands, can be simulated by including suitable markers in the deformable member.

The deformable phantom apparatus can simulate regular and irregular human breathing patterns by adapting the pressure variation in the chamber or in the deformable member accordingly. In the embodiment of the mechanism of motion comprising a moveable wall of the chamber and an actuator, the actuator can be programmed with the appropriate motion pattern or be manually controlled.

One such application of the deformable phantom apparatus of the present invention is in 4-D CT scanning. This is a more recent imaging technique in which the imaging process includes a temporal component which generates sequential image datasets for multiple phases of the breathing cycle of the patient being imaged. Therefore, it is possible through 4-D CT scanning image acquisition to accurately image the tumour and surrounding anatomy, and to quantify the motion of the tumour and surrounding anatomy. The development of 4-D CT has led to the consideration of four-dimensional radiotherapy which is defined as "the explicit inclusion of the temporal changes of anatomy during the imaging, planning and delivery of radiotherapy". Within such a regimen, tumour motion could be accommodated, for example, by tracking tumours in real time and by tailoring the ionizing radiation beam delivery according to the patient's anatomy during a respiratory cycle.

Information about the anatomical deformations can be derived from 4-D CT data combined with a deformable registration algorithm that registers images from different respiratory phases back to a reference respiratory phase. Deformable image registration is the process of applying a geometrical transformation to an image volume in order to align it with another image volume by maximizing a similarity criterion such as pixel intensity and gradient or mutual information. The geometrical transformation provided by the image registration technique is needed for systematic delineation of structures and for dose accumulation (4D dose calculation) on multiple CT datasets acquired at different breathing phases in the 4D treatment planning stage.

Unless otherwise specified, the following definitions apply: The singular forms "a", "an" and "the" include corresponding plural references unless the context clearly dictates otherwise. As used herein, the term "comprising" is intended to mean that the list of elements following the word "comprising" are required or mandatory but that other elements are optional and may or may not be present. As used herein, the term "consisting of" is intended to mean including and limited to whatever follows the phrase "consisting of". Thus the phrase "consisting of" indicates that the listed elements are required or mandatory and that no other elements may be present.

BRIEF DESCRIPTION OF THE DRAWINGS

Further aspects and advantages of the present invention will become better understood with reference to the description in association with the following Figures in which:

FIG. 9 is a front plan view of the deformable phantom apparatus of FIG. 1 when the deformable lung phantom is in (a) a normal state, and (b) a deformed state;

FIG. 10 illustrates an alternative embodiment of the deformable phantom apparatus of FIG. 1 including an alternative embodiment of the deformable lung phantom of FIG. 1 in (a) a normal state, and (b) a deformed state;

FIG. 11 illustrates deformable registration of the deformable lung phantom of FIG. 1 shown on an axial cut: (a) inhale image; (b) exhale image; (c) inhale deformed to the exhale; (d) inhale and exhale shown together before registration; and (e) exhale and deformed inhale shown together after registration;

FIG. 12 illustrates CT images and CT number histograms within the whole lung region of (a) a real lung, and (b) the deformable lung phantom of FIG. 1;

FIG. 13 illustrates a CT image of simulation of vascular and bronchial bifurcations of a lung using the markers of FIGS. 7 and 8 incorporated into the deformable lung phantom of FIG. 1 when viewed (a) axially, and (b) coronally;

DETAILED DESCRIPTION OF THE INVENTION

Figure 1:
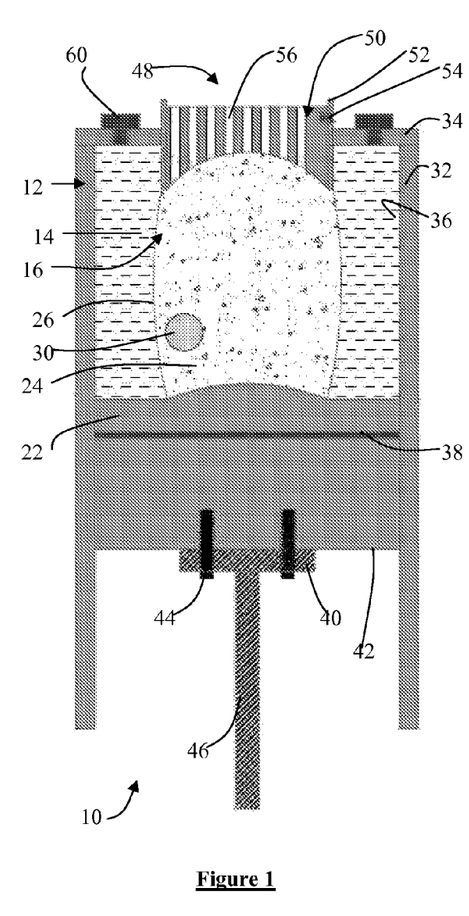
FIG. 1 is a front plan view of a deformable phantom apparatus, including a deformable lung phantom shown in cross-section, according to an embodiment of the present invention.
Figure 2:
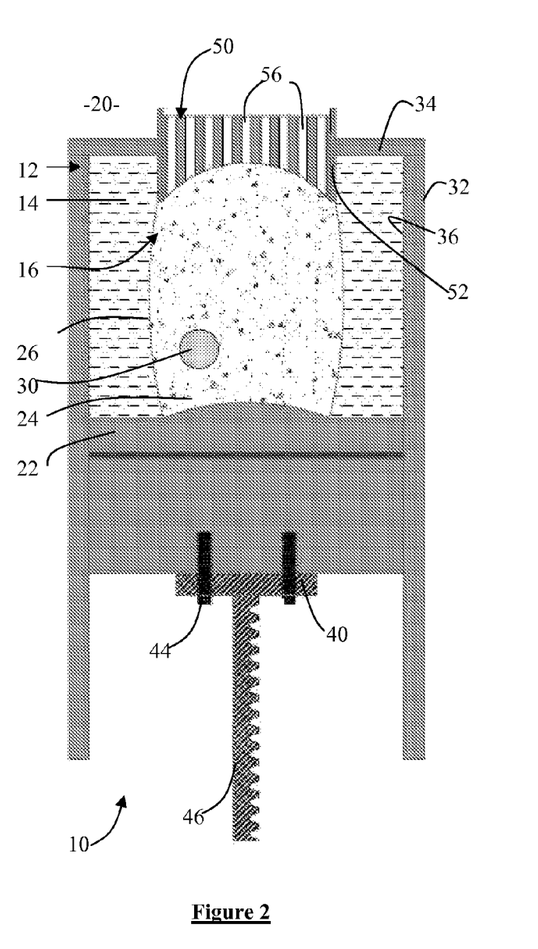
FIG. 2 is a side view of the deformable phantom apparatus of FIG. 1.
Figure 3:
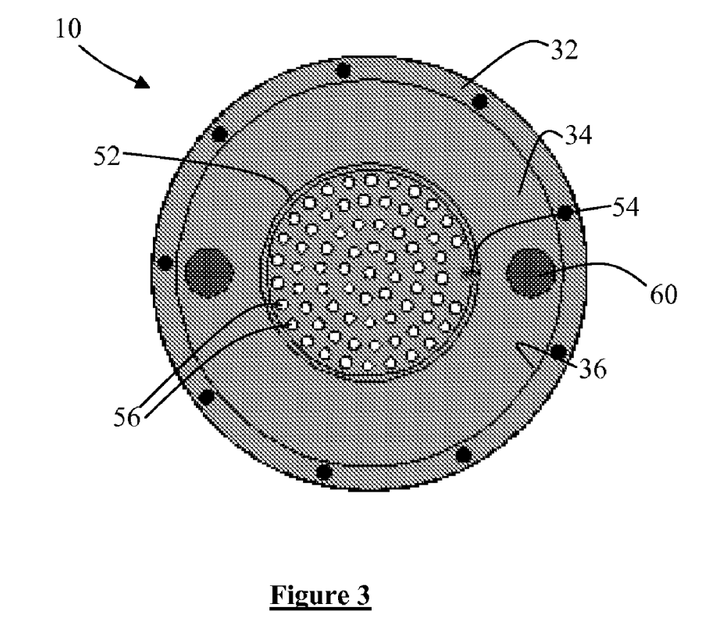
FIG. 3 is a top plan view of the deformable phantom apparatus of FIG. 1.

Referring initially to FIGS. 1 to 3, there is illustrated a deformable phantom apparatus 10 for simulating motion of a patient's anatomy in 3D during breathing. In a broad aspect, the deformable phantom apparatus 10 comprises a chamber 12 fillable with a first fluid 14, a deformable member 16 comprising tissue equivalent material of the anatomy being simulated, the deformable member 16 being positionable within the chamber 12 in the first fluid 14 and having an open end 18 (FIG. 4) in fluid communication with a second fluid 20 outside the chamber 12 in use; and a mechanism for causing the second fluid 20 to flow through the open end 18 to deform the deformable member 16 between a normal state and a deformed (extended or inflated) state to simulate anatomical motion during breathing.

In a preferred embodiment described below, the first fluid 14 is water and the second fluid 20 is air such that the chamber 12 is filled with water and the deformable member 16 is in fluid communication with air outside of the chamber 12 but not in fluid communication with the fluid in the chamber. Air is caused to flow through the open end 18 by adjusting the pressure in the chamber 12. This is achieved by changing the chamber volume by means of a moveable chamber wall 22 to expand and contract the deformable member 16. Moving the chamber wall 22 to increase the chamber volume reduces the pressure on the deformable member 16 and causes the deformable member 16 to expand which simulates inhalation. Reducing the chamber volume increases the pressure on the deformable member 16 causing the deformable member to expel air from the open end 18 and contract which simulates exhalation. This arrangement results in a 3D non-isotropic deformation of the deformable member 16 which can allow tracking of the motion of a simulated organ during respiration.

In the present embodiment, the deformable phantom apparatus 10 is arranged to simulate the movement/deformation of a lung in a thoracic cavity of a human as the human breathes. However, the invention is equally applicable to the simulation of the physiological movement of other organs and structures in or near the thoracic cavity of a human or animal body, or to other organs or structures in other parts of the human or animal body such as the heart or liver.

Figure 4:
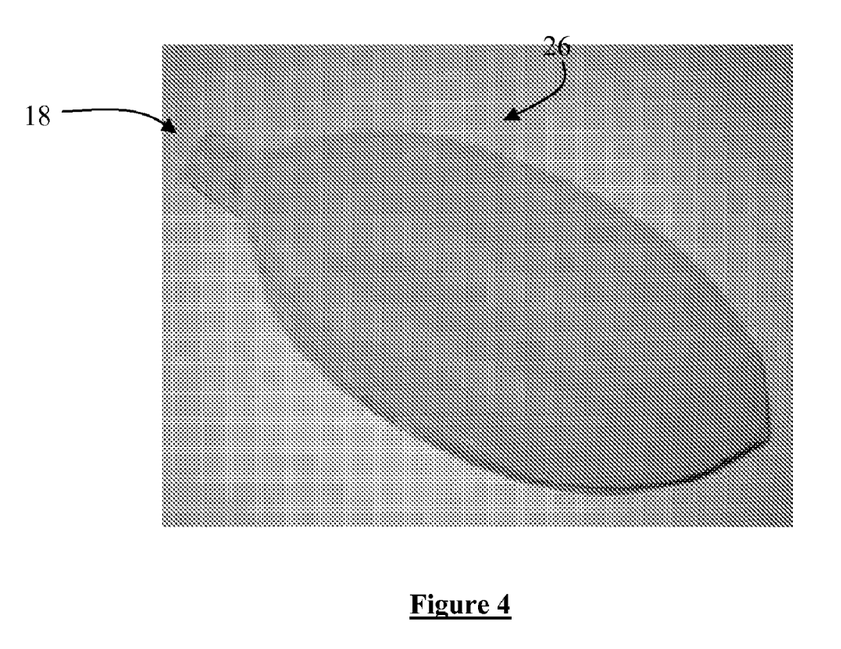
FIG. 4 is a perspective view of a cover portion of an embodiment of the deformable lung phantom of FIG. 1.
Figure 5:
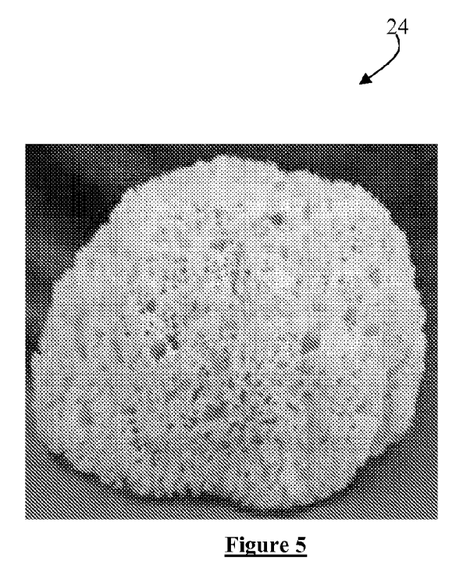
FIG. 5 is a perspective view of a core portion of an embodiment of the deformable lung phantom of FIG. 1.

Referring now to FIGS. 4 to 8, the deformable member 16 (phantom), which is arranged to simulate the lung in this embodiment, comprises a core portion 24 encased by a cover portion 26. The cover portion 26 is a balloon-like sheath and is a deformable, waterproof container having an open mouth at one end, as best seen in FIG. 4. The open mouth 18 of the cover portion 26 defines the open end 18 of the deformable member. The cover portion 26 is made of a rubber, such as natural rubber latex, which can inflate and deflate, but can also be made of any other deformable material such as a plastic which can contain the core portion 24. Preferably the core portion 24 comprises a resilient, compressible material which can expand and retract to its original size and shape. The core portion 24 is a deformable, lung tissue equivalent material such as, for example, sponge material shown in FIG. 5. It has been found that slightly dampened natural yellow sponge satisfactorily simulates the radiological properties of lung tissue in terms of its density, atomic number and electron density and hence the desired Hounsfield (CT) numbers on computed tomography. However, other materials can be used for the core portion 24 such as foams, gels, latex foams, natural rubber foam etc. which can be adapted or combined according to the imaging application with which the deformable phantom apparatus 10 of the present invention is to be used and the anatomy which is to be simulated. In this embodiment, the cover portion 26 and the core portion 24 in their natural, unextended states have about a 15 cm diameter. The core portion 24 can comprise a single item or a plurality of items, such as five pieces of slightly dampened natural yellow sponge used in this embodiment.

Figure 6:
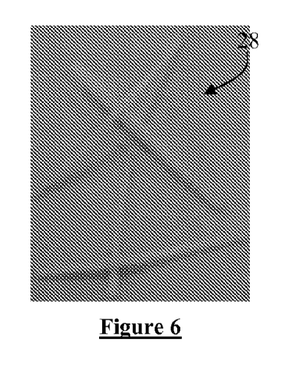
FIG. 6 is a perspective view of a needle-type marker of the deformable lung phantom of FIG. 1.
Figure 7:
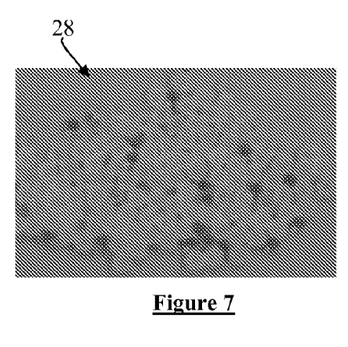
FIG. 7 is a perspective view of a particulate-type marker of the deformable lung phantom of FIG. 1.
Figure 13A:
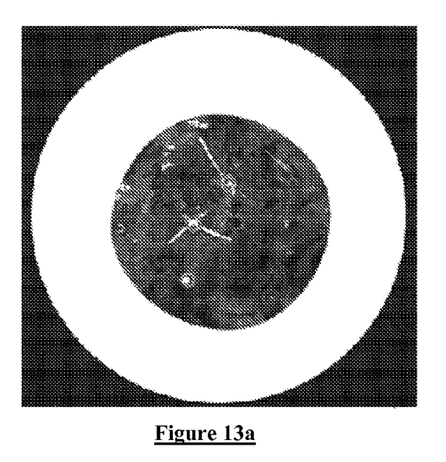
Figure 13B:
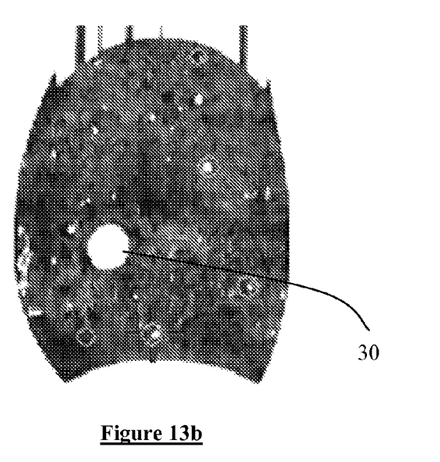
Figure 15:
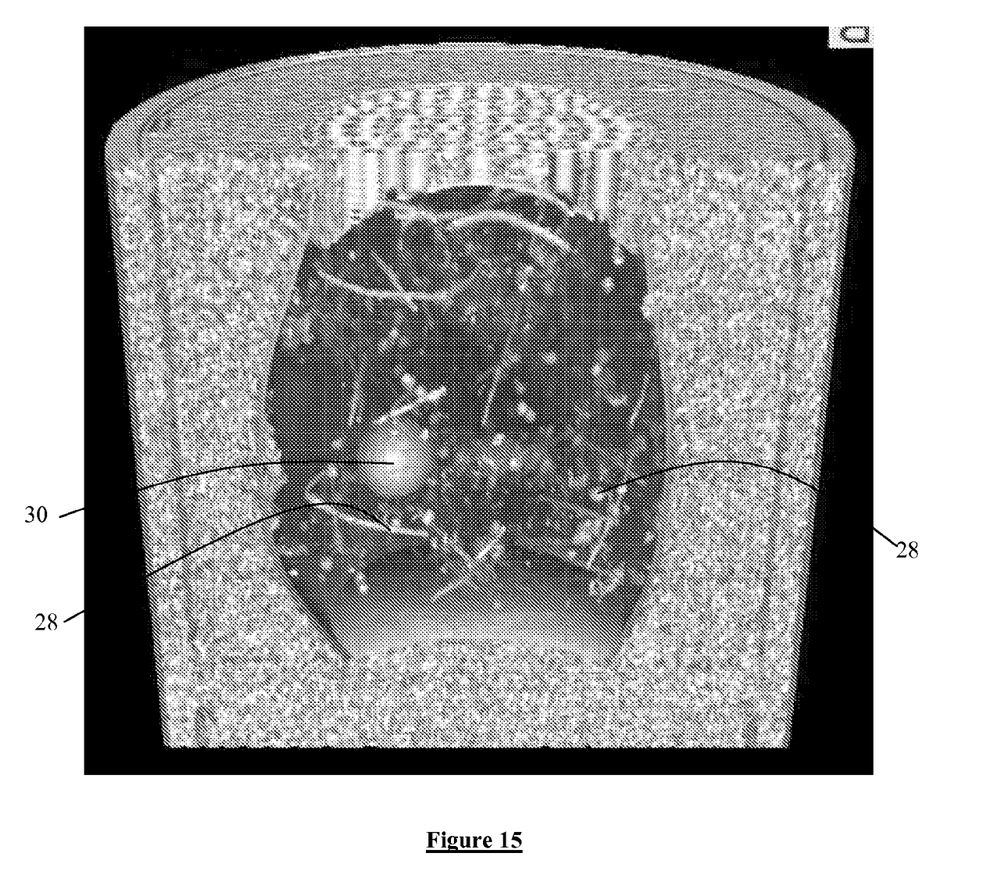
FIG. 15 is a 3D rendering of computed tomographic images of the deformable lung phantom of FIG. 1 demonstrating the distribution of features (tumour and markers) inside the deformable lung phantom.

Markers 28 are placed within the core portion 24 of the deformable phantom 16 to serve as landmarks for deformable image registration procedure applied in 4D radiotherapy treatment, or other treatment, planning processes. These markers 28 are elongate strands (FIG. 6) and spherical beads (FIG. 7) which simulate the vascular and bronchial bifurcations of a lung. The elongate strands may be made of Nylon™ and the spherical beads of Plexiglas™. These markers 28 are substantially uniformly placed throughout the volume of the material of the core portion 24 and attached in place, such as by adhesive or the like (not shown). These markers 28 can be seen in the axial and coronal views of a computed tomography of the deformable phantom 16 (FIGS. 13 and 15). This allows deformable image registration of 4D CT images of the phantom, which is an important tool in the 4D treatment planning process. Other shapes and sizes of markers 28 may be chosen appropriate to the anatomy of the patient which is being simulated and the imaging application. The markers 28 may also be integral with a portion of the deformable phantom 16 such as the cover portion 26.

Figure 9A:
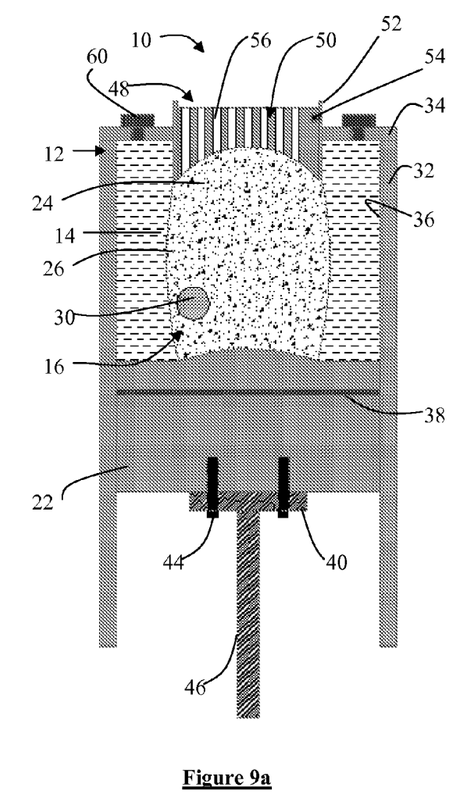
Figure 9B:
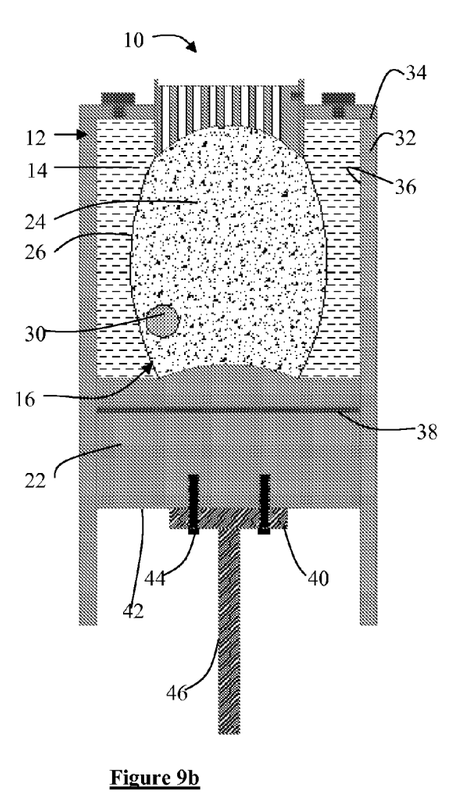

The deformable phantom 16 optionally contains a deformable mass 30 (a tumour phantom) which simulates a tumour or lesion in the organ or anatomy simulated by the deformable phantom 16. The tumour phantom 30 is placed within the core portion 24 of the deformable phantom 16 to replicate the presence and movement of a tumour within the lung phantom (as can be seen in FIGS. 1, 2 and 9) and is held in place by adhesive or the like (not shown).

Figure 8:
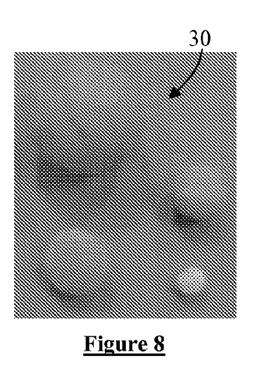
FIG. 8 is a perspective view of a tumour portion of the deformable phantom of FIG. 1.

The tumour phantom 30, shown in FIG. 8, is deformable and is made of a tumour tissue or lesion equivalent material, such as for example, Dermasol™ having a density of 0.818 g/cm$^3$ (FIG. 8). Dermasol™ is a medical device material made from Thermoplastic Elastomer (TPE) manufactured by California Medical Innovation (CMI). The tumour phantom 30 may have at least one opening, preferably two small incisions, to hold a radiation detector (not shown) such as, for example, radiochromic film (e.g. Gafchromic EBT, etc) for monitoring the received levels of radiation. Gafchromic film is tissue equivalent (atomic number in the range of 6 to 6.5), self developing, insensitive to visible light so that it can be easily cut to any shape. The film can be placed in the tumour phantom 30 before imaging of the deformable phantom 16 and can stay in place up to and during the exposure of the phantom in the radiation treatment beam.

Tumour phantoms 30 of various sizes, shapes and densities can be placed within the deformable phantom 16 chosen according to the clinical situation. Three-dimensional radiation dose measurements can be achieved by placing the film in several planes within the tumour phantom 30. In addition, point measurements can be performed throughout the phantom with ionization chambers, thermoluminescent detectors, metal oxide field-effect detectors or other radiation detectors that may provide positional information.

In use, the markers 28 and optionally the tumour phantom 30 are positioned in the core portion 24. The core portion 24 is compressed and pushed through the open mouth 18 of the cover portion 26 to situate the core portion 24 within the cover portion 26 and form the deformable phantom 16. Preferably, the amount of core portion material in the cover portion 26 is such that when the phantom expands, the core portion 24 completely occupies the additional space created in the phantom 16 i.e. when the cover portion 26 is in its most expanded state, the material of the core portion 24 still abuts and pushes against an inner wall of the cover portion 26. Otherwise, it has been found that air pockets can form within the cover portion 26 which represents an unrealistic simulation of the real situation.

Referring back to FIGS. 1 to 3, the chamber 12 of the deformable phantom 16 apparatus 10, which simulates the thoracic cavity in this embodiment, is cylindrical in shape and has an open top end and an open bottom end, before assembly, and a side wall 32. The chamber 12 may be made of Perspex™, or any other suitable material. The top end can be sealed by a removable lid 34. The bottom end can be sealed by a removable bottom wall (moveable chamber wall) 22 which can be caused to slide against an inner face 36 of the chamber side wall 32 to move towards or away from the chamber top end. The bottom wall 22 is provided with an o-ring 38 around its circumference to provide a water-proof sealing engagement with the side wall 32 of the chamber 12.

A piston plate 40 is attached to an outer face 42 of the bottom wall 22 by screws 44 or the like. A piston rod 46 extends from the piston plate 40 away from the bottom wall 22. The piston rod 46 can be made of a metallic material and have teeth along one edge. Movement of the piston rod 46, plate 40 and bottom wall 22 is driven by a motor (not shown) in a manner which will be clear to a skilled person and so will not be described further. Any other motion actuator can be used instead of a motor and the mechanical arrangement adapted accordingly. The movement of the bottom wall 22 can be variable and can be programmable to replicate breathing patterns which may be regular or irregular with varying periods and amplitudes. The breathing pattern may be specific to a patient and based on his or her actual breathing patterns. Typically, in simulating a breathing pattern having an inhale/exhale rate of 10 to 15 per min, the inhale state is simulated by a piston retraction of 10 to 30 mm relative to the exhale.

The lid 34 of the chamber 12, best seen in FIGS. 1 to 3, can be received into the open top end of the chamber 12 and fixed in place, relative to the chamber side wall 32, by screws or the like. The lid 34 comprises an o-ring (not shown) around its circumference to form a water-tight seal with the chamber side wall 32. The lid 34 comprises an opening 48 in substantially its central portion for receiving a perforated end piece 50. The opening 48 is defined by a rim 52 which extends either side of the lid 34 so that when the lid 34 is positioned at the top end of the chamber 12, one end of the rim extends into the chamber 12 and the other end away from the chamber 12 to form an inner cylinder extending partially into the chamber 12. In use, the mouth 18 of the cover portion 26 is stretched over the portion of the rim 52 extending into the chamber 12 and is secured in that position by adhesive or a suitable mechanical clamping arrangement (not shown).

The perforated end-piece 50 can be removably positioned in the lid opening 48 within the inner cylinder and can be fixed in position relative to the inner chamber by a screw 54 or the like. The perforated end-piece 50 comprises at least one opening 56 which functions as a passageway or conduit for fluid communication of a volume of air or other fluid into and out of the deformable phantom 16 in use and also keeps the core portion 24 in place inside the cover portion 26. The number, size and shape of the openings 56 within the perforated end-piece 50 can vary from that illustrated in FIGS. 1 to 3. The lid 34 also comprises at least one smaller opening 58 through which fluid can be passed into or out of the chamber 12 and which can be sealed by a cap 60 or the like. Two smaller openings are provided in the embodiments of FIGS. 1-3, 9 and 10 although there could be more or less than two.

The deformable phantom apparatus 10 is assembled by first assembling the deformable phantom 16 by placing the sponge material or other tissue-equivalent material forming the core portion 24 inside the cover portion 26. The deformable phantom 16 is then mounted inside the chamber 12 by attaching the end of the cover portion 26 opposite to the mouth 18 to an inside face 62 of the bottom wall 22 by adhesive or suitable mechanical clamp arrangements (not shown). The mouth 18 of the cover portion 26 is stretched over a portion of the rim 52 and secured in place to attach the deformable phantom 16 to the lid 34. The lid 34 is then positioned over the open top end of the chamber 12 and sealingly fixed in place. The perforated end-piece 50 is positioned in the inner cylinder defined by the rim 52 and fixed in place. The space around the deformable phantom 16 in the chamber 12 is filled with a volume of fluid, preferably non-compressible fluid such as water, which replicates the chest mass in the thoracic cavity. The apparatus 10 is positioned to replicate the position of a reclined patient in a CT scan apparatus. So, in this embodiment, the chamber 12 is oriented so that its side wall 32 are substantially parallel with the floor and is laid on a scan bed of the CT scan apparatus. Of course, the orientation can be adapted according to the application and it will be appreciated that the invention could work regardless of orientation.

In use, the motor drives movement of the bottom wall 22 of the chamber 12 of the assembled phantom apparatus 10. In the resting position (FIGS. 1, 2 and 9a) the pressure within the deformable phantom 16 and within the chamber 12 is in an equilibrium state. During piston rod 46 retraction, the bottom wall 22 is caused to move away from the lid 34 of the chamber 12 from the resting position (FIG. 9a) to a retracted position (FIG. 9b). As one end of the deformable phantom 16 is attached to the bottom wall 22 and the other end to the lid 34, this causes the deformable phantom 16 to elongate and the chamber volume to increase which simulates elongation of the thoracic cavity during inhalation. As a result, air is caused to enter the deformable phantom 16 through the openings 56 of the perforated end-piece 50 of the lid 34. This causes the cover portion 26 to expand which allows the sponge material of the core portion 24 to decompress. The shroud (layer) of water of constant volume surrounding the deformable phantom 16 becomes thinner in cross-section and elongated in this deformed state. This arrangement results in a realistic 3D non-isotropic deformation of the phantom 16, including the phantom tumour 30 and the markers 28, which is similar to a real lung during breathing.

When the bottom wall 22 is pushed back towards the chamber lid 34, the deformable phantom 16 returns to its resting (normal) state which simulates exhalation.

Additionally, by blocking one or more of the passages 56 in the perforated end-piece 50, or by regulating the flux of air in and out of the lid 34 using valves (not shown), for example, one can achieve simulation of the hysteresis of a tumour's movement as the deformable phantom 16 expands and contracts.

In this way, movement of the piston rod 46 and the bottom wall 22 according to a rate matching a patient's breathing can replicate the movements of a lung, or other organ or anatomy, during breathing. By means of this arrangement, the deformable phantom 16 can deform in three-dimensions and in a similar manner (non-isotropically) to that of a human anatomy during breathing. Imaging data can be acquired of the deformable phantom 16 during simulated breathing. Therefore, by means of one embodiment of the deformable phantom apparatus 10 of the present invention, the distortion of the radiation dose in a deforming lung can be simulated. Therefore, accurate radiation dose measurements can be achieved and the effect of photon-electron interactions in deforming geometries, which are often overseen, can be accounted for.

Figure 10A:
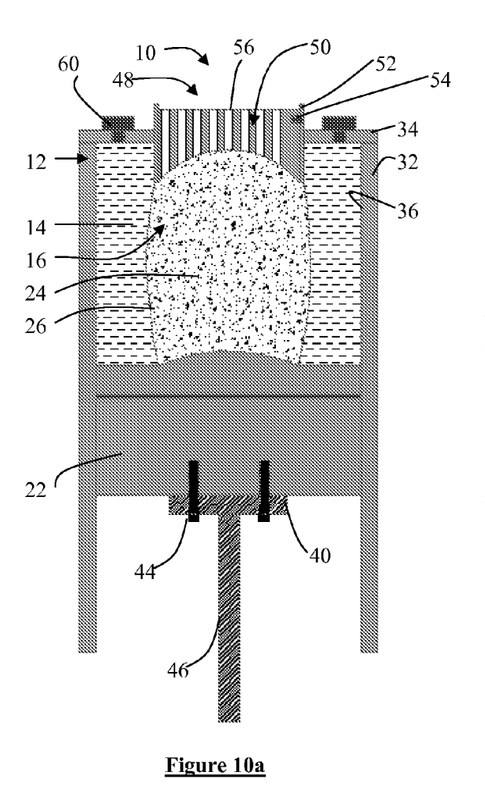
Figure 10B:
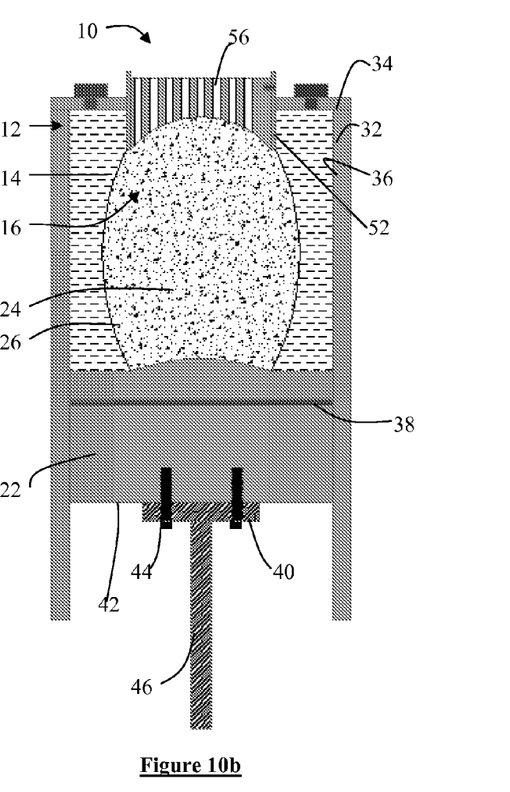

An alternative embodiment is illustrated in FIG. 10 in which the deformable phantom 16 differs from that of FIGS. 1, 2 and 9 in that a tumour phantom is not included.

The deformable phantom apparatus 10 of the present invention has many uses. For example, by obtaining 4D CT images of the deformable phantom apparatus 10 in use, 4D CT procedures for irregular breathing patterns can be evaluated and validated. The accuracy of deformable registration can be evaluated using the markers 28 inside the deformable phantom 16. Real-time tumour localization and tracking devices can be tested and calibrated. Dose delivery can be measured taking into account the change in lung volume during the breathing cycle including distortions of the dose distribution due to the deforming phantom. 4D-optimized treatment plans which incorporate the effects of breathing motion can be evaluated. 4D dose calculation algorithms in deformable/moving targets can be validated. Individual patient treatment plans can be verified dosimetrically and positionally before treatment with motion mitigation techniques. The deformable phantom apparatus 10 can also be miniaturized to form an insert in a larger anthropomorphic phantom used for quality assurance procedures in radiotherapy. Also, existing phantom devices can be adapted to employ principles of embodiments of the present invention e.g. the rigid Rando® anthropomorphic phantom (manufactured by The Phantom Laboratory, NY, USA).

Moreover, validation of any 4D radiation dose calculation algorithm in a moving/deformable tumour is possible by a direct comparison of the calculated dose to the actual measured dose received by the tumour. Therefore, the deformable phantom apparatus 10 provides a means of quantitative verification and comparison between a conventional treatment plan, a 4D cumulative dose treatment plan and the actual measured radiation dose received by the target.

By injecting a radioactive substance in the tumour, the phantom can also be used for the evaluation of respiratory motion effects during Positron Emission Tomography (PET) image acquisitions and validation of 4D PET procedures for irregular breathing patterns.

In one use of the present invention, the phantom apparatus 10 is used for quality assurance of adaptive (4D) or non-adaptive radiotherapy delivery. The steps of this process are as follows:

acquiring 4D CT datasets of the deformable phantom apparatus 10 containing dosimeters within the tumour phantom 30;

determining the deformable transformation between each breathing state and the reference state, which can be the exhale state (see FIG. 11);

contouring anatomy and determining dosimeter location on the reference state and transforming them to the other breathing datasets using the deformable transformation from the previous step;

creating treatment plans for each image dataset corresponding to each breathing state (adaptive delivery) or creating a single treatment plan on the reference state (non-adaptive delivery) and transforming dose distributions back to the reference state;

delivering the plan if found acceptable; and comparing dosimeter readouts to plan dose calculation and assessing acceptability.

A skilled person will appreciate that alternative uses of embodiments of the present invention are possible which can include known methods of assessing dynamic phantom data for radiotherapy.

Example: In one example of the first embodiment of the present invention, the height of the bottom wall 22 was 100 mm and the chamber 12 was about 400 mm high. The outer diameter of the chamber 12 was about 228 mm and the side wall 32 had a thickness of about 12.5 mm. The diameter of the central portion was about 108 mm and the thickness of the rim was 6 mm. The bottom wall 22 of the cylinder was about 100 mm thick and was made of Plexiglas™. Piston travels of up to 40 mm were achieved. Although significantly larger diaphragm motions can be programmed (up to 40 mm), the displacements/deformations in initial tests with the deformable phantom apparatus 10 were: superior/inferior (S/I) 20 mm, anterior/posterior (A/P) 4 mm and left/right (L/R) 5 mm.

Figure 11A:
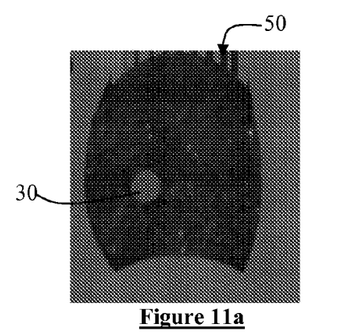
Figure 11B:
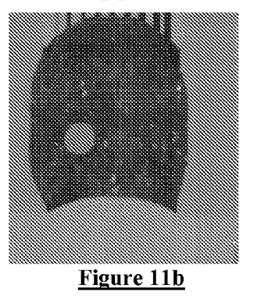
Figure 11C:
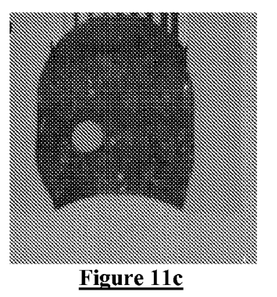
Figure 11D:
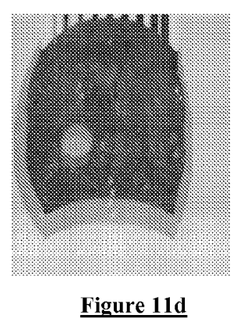
Figure 11E:
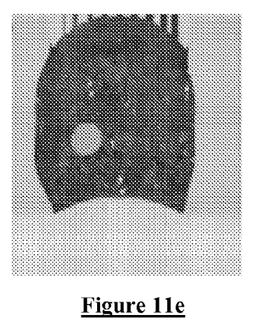
Figure 12A:
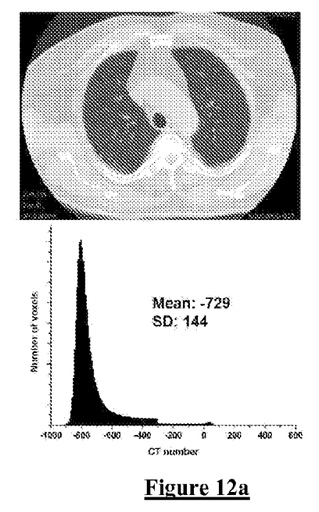
Figure 12B:
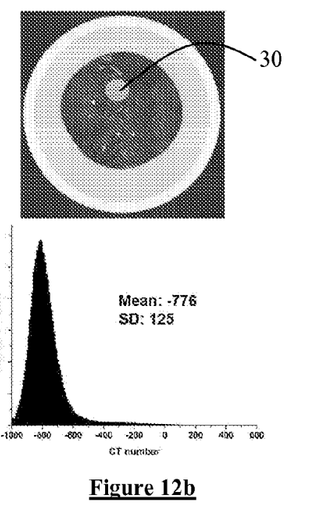

FIG. 11 demonstrates the deformable registration of coronal images of the phantom 16 in which the lung features (markers 28) are used: at peak inhalation (FIG. 11a showing inhale image in red and FIG. 11b showing exhale in green), at peak exhalation (FIG. 11c) when peak inhalation is deformed to peak exhalation, with peak-inhalation and peak-exhalation together before registration (FIG. 11d), and peak exhalation and deformed peak inhalation shown together after registration (when overlapping, structures that are not perfectly matched appear green or red) (FIG. 11e). FIG. 12 demonstrates the radiological similarities between the images from the lung phantom apparatus 10 and a real lung based on computed tomography images. The resulting average and spread in CT numbers for the artificial lung simulated by the deformable phantom apparatus 10 were comparable to those of a real lung. Table 1 shows a comparison of mass densities for a real lung and the deformable phantom apparatus 10 of the present invention.

TABLE 1

Comparison of mass density and diaphragm movement of the deformable phantom 16 with equivalent features in a real human lung (data for the real lung taken from Rojano Kashani, et al, "Technical note: A deformable phantom for dynamic modeling in Radiation Therapy", Med. Phys. 34 (1), Jan. 2007).

|  | Diaphragm movement (mm) | Density (g/cm$^3$) |
| --- | --- | --- |
| Real lung (EOI) |  | 0.21 |
| Real lung (EOE) | 13 | 0.23 |
| Phantom lung (EOI) |  | 0.19 |
| Phantom lung (EOE) | 20 | 0.24 |

Figure 14:
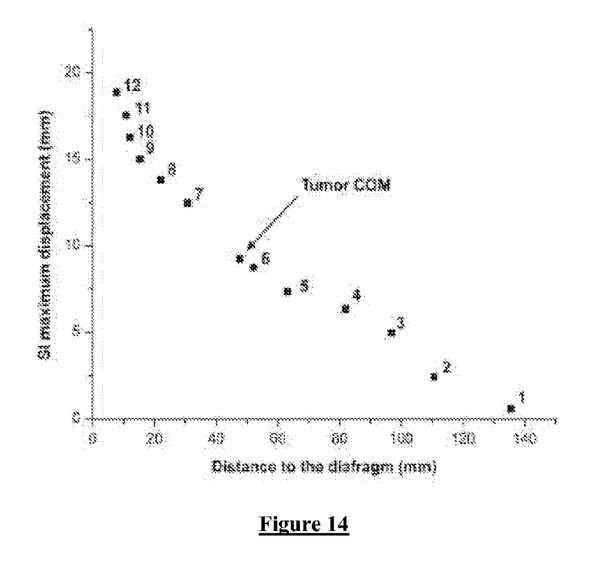
FIG. 14 is a graph illustrating superior-inferior (SI) maximum displacements of some of the markers of FIG. 13 along the longitudinal axis as a function of their initial distance to the diaphragm for a 20 mm movement of a piston of the deformable phantom apparatus of FIG. 1.

The 3D trajectory of different points (determined by the markers 28) in the deformable phantom 16 over a complete breathing cycle was determined. These features, uniformly placed throughout the volume of the sponge material, can be seen in the axial and coronal views of a computed tomography of the phantom (FIGS. 13a and 13b) and also in FIG. 15 which demonstrates a 3D rendering of the phantom 16. The magnitude of motion at different locations of the phantom 16 is related to their distance to the diaphragm which accurately mimics the situation in a real lung (FIG. 14). Repeat imaging of the phantom at different piston positions, corresponding to different breathing phases, demonstrated a very good motion reproducibility of the selected features inside the phantom. The accuracy of deformable image registration on the deformable phantom apparatus 10 was evaluated to be 0.5 mm (0.4 mm SD). The accuracy of the deformable registration between the reference planning dataset and scans taken at different breathing phases may have an important effect on the accuracy of the calculation of the cumulative dose.

It should be appreciated that the invention is not limited to the particular embodiments described and illustrated but includes all modifications and variations falling within the scope of the invention as defined in the appended claims.

For example, the mechanism causing the deformable phantom 16 to expand and contract may comprise a suitable mechanism to force air or another fluid in and out of the deformable phantom 16 through the open end 18. Also, the deformable phantom 16 need not be attached to the bottom wall 22 of the chamber 12, although it has been found that such an attachment provides an anthropomorphic non-isotropic expansion of the deformable phantom. In this respect, the deformable phantom 16 may be attached, by its mouth, only to the lid 34 or to another portion of the apparatus 10, as long as the mouth of the deformable phantom 16 is in fluid communication with a fluid outside of the chamber 12 e.g. air. The chamber 12 may be filled with any other suitable fluid other than water. Any other suitable device which can restrict or vary the opening of the open end of the deformable member can be used instead of the perforated end-piece. The deformable phantom may be one-piece instead of having a cover portion and a core portion.

What is claimed is:

1. A deformable phantom apparatus for simulating motion of a patient's anatomy in 3D during breathing, the apparatus comprising:

a chamber fillable with a first fluid, a deformable member comprising tissue equivalent material of the anatomy being simulated, the deformable member being positionable within the chamber in the first fluid and having an open end in fluid communication with a second fluid outside the chamber in use; and a mechanism for causing the second fluid to flow through the open end to deform the deformable member between a normal state and a deformed state to simulate motion during breathing.

2. A deformable phantom apparatus according to claim 1, wherein the deformable member includes at least one marker having a different imaging property than the tissue equivalent material.

3. A deformable phantom apparatus according to claim 1, wherein the deformable phantom comprises a core portion and a cover portion, the core and cover portions being deformable.

4. A deformable phantom apparatus according to claim 3, wherein the core portion is a porous material which is in a compressed state in the cover portion when the deformable member is in the normal state.

5. A deformable phantom apparatus according to claim 4, wherein the porous material is a spongey material.

6. A deformable phantom apparatus according to claim 1, wherein the mechanism comprises a moveable wall of the chamber connectable to an actuator to drive movement of the moveable wall to cause the second fluid to flow through the open end of the deformable member.

7. A deformable phantom apparatus according to claim 6, further comprising an actuator connectable to the moveable wall.

8. A deformable phantom apparatus according to claim 6, wherein the deformable phantom is attachable to the moveable wall of the chamber such that the deformable phantom is elongated in at least one direction in the deformed state.

9. A deformable phantom apparatus according to claim 1, wherein the deformable member further comprises a deformable mass for simulating a tumour or a lesion, the deformable mass being positionable in the tissue equivalent material.

10. A deformable phantom apparatus according to claim 9, further comprising a radiation detector locatable in the deformable mass for radiation measurements.

11. A deformable phantom apparatus according to claim 1, wherein the first fluid is a liquid.

12. A deformable phantom apparatus according to claim 11, wherein the liquid is water.

13. A deformable phantom apparatus according to claim 1, wherein the second fluid is a gas.

14. A deformable phantom apparatus according to claim 13, wherein the second fluid is air.

15. A deformable phantom apparatus according to claim 1, wherein the patient's anatomy being simulated is within or around the thoracic cavity.

16. A deformable apparatus according to claim 15, wherein the patient's anatomy is a lung.

17. A deformable phantom apparatus for simulating motion of a patient's lung in 3D during breathing, the apparatus comprising:
a chamber fillable with a first fluid,
a deformable lung phantom comprising lung tissue equivalent material, the lung phantom being positionable within the chamber in the first fluid and having an open end in fluid communication with a second fluid outside the chamber in use; and
a mechanism for varying the pressure in the chamber or in the lung phantom to cause the second fluid to flow through the open end to deform the lung phantom between a normal state and a deformed state simulating lung motion during breathing.

18. A deformable phantom apparatus according to claim 17, wherein the lung phantom includes at least one marker having a different imaging property than the tissue equivalent material, the at least one marker simulating the vascular and bronchial bifurcations of the lung.

19. A deformable phantom apparatus according to claim 17, wherein the lung phantom comprises a core portion and a cover portion, the core and cover portions being deformable.

20. A deformable phantom apparatus according to claim 19, wherein the core portion is a porous material which is in a compressed state in the cover portion when the lung phantom is in the normal state.

21. A deformable phantom apparatus according to claim 17, wherein the mechanism comprises a moveable wall of the chamber connectable to an actuator to drive movement of the moveable wall to vary the pressure in the chamber.

22. A deformable phantom apparatus according to claim 21, further comprising an actuator connectable to the moveable wall.

23. A deformable phantom apparatus according to claim 17, wherein the lung phantom is attachable to the moveable wall of the chamber so that the lung phantom is elongated in at least one direction in the deformed state.

24. A deformable phantom apparatus according to claim 17, wherein the lung phantom further comprises a deformable mass for simulating a tumour or a lesion, the deformable mass being disposed in the tissue equivalent material and being movable between the normal and deformed states of the lung phantom.

25. A deformable phantom apparatus according to claim 24, further comprising a radiation detector locatable in the deformable mass for dose measurements.

26. A deformable phantom apparatus according to claim 17, wherein the first fluid is water and the second fluid is air.

27. A deformable phantom apparatus according to claim 17, further comprising a perforated end-piece receivable in the open end of the lung phantom.

28. A deformable phantom comprising tissue equivalent material, the lung phantom being positionable within a chamber filled with a first fluid and having an open end in fluid communication with a second fluid outside the chamber in use; wherein the deformable phantom is configured to move between a normal state and a deformed state as pressure in the chamber or in the deformable phantom is varied, to simulate lung motion during breathing.

29. A deformable phantom according to claim 28, comprising a core portion and a cover portion, the core and cover portions being deformable.

30. A deformable phantom according to claim 29, wherein the core portion is a porous material which is in a compressed state in the cover portion when the deformable member is in the normal state.

31. A deformable phantom according to claim 28, wherein the cover portion is a rubber balloon and the core portion is a spongey material.

32. A deformable phantom according to claim 28, including at least one marker positionable within the tissue equivalent material and having a different imaging property than the tissue equivalent material.

33. A deformable phantom according to claim 28, including at least one deformable mass positionable within the tissue equivalent material for simulating a tumour or a lesion.

* * * * *